United States Patent [19]

Conciatori et al.

[11] 4,440,945

[45] Apr. 3, 1984

[54] ANISOTROPIC HEAT-CURABLE ACETYLENE-TERMINATED MONOMERS AND THERMOSET RESINS PRODUCED THEREFROM

[75] Inventors: Anthony B. Conciatori, Chatham; Eui W. Choe, Randolph; Gerald Farrow, New Providence, all of N.J.

[73] Assignee: Celanese Corporation, New York, N.Y.

[21] Appl. No.: 399,609

[22] Filed: Jul. 19, 1982

[51] Int. Cl.³ ..................... C07C 69/82; C07C 69/76; C07C 69/80
[52] U.S. Cl. ...................................... 560/86; 526/285; 526/322; 560/64; 560/65; 560/67; 560/73; 560/80; 560/83; 560/85
[58] Field of Search ...................... 560/67, 73, 80, 83, 560/85, 86, 64, 65; 526/322, 285

[56] References Cited

U.S. PATENT DOCUMENTS 4,068,082  1/1978  Stoffey et al. .................... 560/86 X
4,283,551  8/1981  Chow et al. ......................... 560/86

*Primary Examiner*—Glennon H. Hollrah
*Assistant Examiner*—Vera C. Clarke
*Attorney, Agent, or Firm*—Burns, Doane, Swecker & Mathis

[57] ABSTRACT

Novel heat-curable acetylene-terminated monomers are provided which exhibit an optically anisotropic melt phase at a temperature which enables it to undergo melt processing in the formation of molded articles, etc. The monomers are capable of being heat-cured at temperatures in excess of the melt processing temperatures to produce a thermoset self-reinforced composite.

12 Claims, No Drawings

ANISOTROPIC HEAT-CURABLE ACETYLENE-TERMINATED MONOMERS AND THERMOSET RESINS PRODUCED THEREFROM

CROSS-REFERENCE TO RELATED APPLICATIONS

This application is related to U.S. patent application Ser. No. 381,598, filed May 24, 1982, of Anthony B. Conciatori, Eui Won Choe and Gerald Farrow entitled "Anisotropic Heat-Curable Acrylic-Terminated Monomers and Thermoset Resins Produced Therefrom."

BACKGROUND OF THE INVENTION

The present invention is directed to anisotropic heat-curable monomers.

Multi-functional heat-curable monomers are known which can be employed in the production of thermosetting composites such as, for example, epoxy-based compositions. However, one disadvantage with such known thermosetting compositions is that they tend to shrink to an undesirable degree subsequent to the cross-linking reaction.

U.S. Pat. No. 4,283,551 (issued to Chow et al) discloses acetylene-terminated polyesters which are prepared by reacting a hydroxyphenylacetylene with a diacid chloride of an aromatic dibasic acid such as 4,4'-benzophenone dicarboxylic acid dichloride. However, the polyesters disclosed therein are stated to have curing temperatures which are disadvantageously high (i.e., on the order of 250° to 400° C.).

It is therefore desirable to provide heat-curable monomers which can be employed in the production of thermosetting resins and which exhibit a reduced tendency to shrink upon curing.

It is also desirable to provide heat-curable monomers which exhibit self-reinforcing characteristics as a result of molecular orientation in the cross-linked resin.

It is also desirable to provide a heat-curable monomer which can be cured at desirably low temperatures.

SUMMARY OF THE PRESENT INVENTION

In accordance with the present invention, there are provided novel heat-curable acetylene-terminated monomers capable of forming an anisotropic melt phase of the formula:

wherein Ar is a divalent radical comprising at least one aromatic ring and $Ar_1$ is a divalent radical selected from the group consisting of phenylene, naphthylene, biphenylene and mixtures thereof.

In accordance with another aspect of the present invention, there are provided cross-linked polyester resins comprised of the above-described monomers.

DETAILED DESCRIPTION OF THE INVENTION

It has been surprisingly and unexpectedly discovered that the heat-curable monomers of the present invention can be employed with significant advantage in the production of thermosetting polyester resins which would be expected to exhibit reduced shrinkage subsequent to being cured. Such a potential advantage is believed to be due to the fact that such monomers are capable of forming an anisotropic melt phase upon being heated to the melting temperature of the monomer. In addition, the monomers of the present invention are capable of being cured at desirably low temperatures to form a thermoset resin.

Unlike monomers commonly encountered in the prior art, the monomers of the present invention are capable of forming an anisotropic melt phase whereby an atypical degree of order is manifest in the molten monomer. The monomer readily forms liquid crystals in the melt phase and accordingly exhibits a high tendency for the monomer chains to orient in the shear direction, with such anisotropic properties being exhibited at temperatures which are amenable for melt processing to form shaped articles. Such order in the melt may be confirmed by conventional polarized light techniques whereby crossed polarizers are utilized. The anisotropic melt phase may be confirmed by the use of a Leitz polarizing microscope at a magnification of 40X with the sample on a Leitz hot stage and under nitrogen atmosphere. The monomer melt is optically anisotropic, i.e., it transmits light when examined between crossed polarizers. The amount of light transmitted increases when the sample is optically anisotropic even in the static state.

The monomers of the present invention can be denoted by the formula:

wherein Ar is a divalent radical comprising at least one aromatic ring and $Ar_1$ is a divalent radical selected from the group consisting of phenylene, naphthylene, biphenylene and mixtures thereof.

By way of example, the divalent radical Ar may include but is not limited to the following:

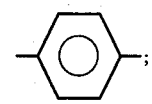
(I)

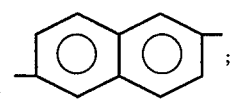
(II)

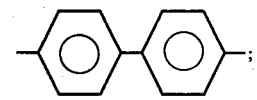
(III)

and

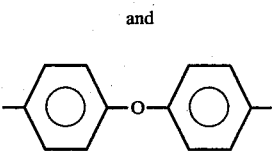
(IV)

At least some of the hydrogen atoms present upon one or more of the aromatic rings in the divalent radicals Ar and $Ar_1$ optionally may be replaced by a substituent selected from the group consisting of an alkyl group of 1 to 4 carbon atoms, an alkoxy group of 1 to 4 carbon atoms, halogen, phenyl, substituted phenyl and mixtures thereof, provided such substitution does not ultimately prevent the monomer from forming an anisotropic melt phase. It is recognized, however, that such substitution may alter the temperature at which the phase transitions occur for the monomer (i.e., the transition from a solid to an anisotropic melt and from an anisotropic melt to a polymerized/cross-linked composition).

More specifically, the monomers of the present invention may include but are not limited to bis(p-carbepropynoxyphenyl)terephthalate; 2,6-bis-(p-carbepropynoxyphenyl)naphthalate; 4,4'-bis-(p-carbepropynoxyphenyl)biphenyldicarboxylate; 4,4'-bis-(p-carbepropynoxyphenyl)oxybiphenyldicarboxylate; bis(p-carbepropynoxyphenyl)methylterephthalate; and bis(p-carbepropynoxyphenyl)chloroterephthalate.

As noted previously, the monomers of the present invention are capable of forming an anisotropic melt phase upon being heated to the necessary phase transition temperature. The monomers will retain such anisotropic characteristics upon being heated to increasingly higher temperatures whereupon the monomer will begin to polymerize and/or cross-link and form a thermosetting polymeric resin at a temperature in excess of the melting temperature of the monomer. The resin advantageously retains the high degree of orientation exhibited by the monomer molecules prior to such polymerization, with the orientation of the molecules in the resin providing a self-reinforcing effect.

Exemplary phase transition temperatures for an exemplary novel monomer of the present invention are set forth below in Table I:

TABLE I

| Monomer | Phase Transitions of Exemplary Anisotropic Multifunctional Monomer | |
|---|---|---|
| | Transition Temperature from Solid to Anisotropic Melt | Transition Temperature from Anisotropic Melt to Polymerization |
| Ar and Ar₁ are phenylene | 113° C. | 210° C. |

The monomers of the present invention may be formed by a variety of ester-forming techniques such as, for example, whereby bis-(carboxyphenyl)terephthalate and a suitable acetylene-terminated moiety possessing hydroxyl groups are reacted which, upon condensation, form the requisite monomer. The acid and the difunctional aromatic moiety are reacted in a molar ratio of about 2:0.5 to 2:1. The organic monomer compounds may be reacted in the absence of a heat exchange fluid via a melt acidolysis procedure. They, accordingly, may be heated initially to form a melt solution of the reactants with the reaction continuing as said polymer particles are suspended therein. A vacuum may be applied to facilitate removal of volatiles formed during the condensation (e.g., acetic acid).

The monomers of the present invention can be molded or otherwise melt processed and then heat cured to yield a polymerized composite of high strength due to the self-reinforcing characteristics of the oriented molecules. The composite will also exhibit desirable thermal and chemical stability. The monomers can be melt processed to form a variety of shaped articles by conventional extrusion and injection molding techniques. Such molding compositions may optionally include various types of fillers (e.g., talc) in amounts of about 1 to 60 percent by weight as well as various types of reinforcing agents (e.g., glass fibers) in amounts of about 1 to 60 percent by weight.

The monomers of the present invention may also be employed as protective coatings on various substrates in the form of the cross-linked resin. The monomers can also be employed as the matrix material for a web of infusible fibers such as glass fibers wherein the monomer is applied to the web in an anisotropic melt state and subsequently heat-cured. Such methods are well known in the art and will not be discussed in greater detail herein.

The invention is additionally illustrated in connection with the following Example which is to be considered as illustrative of the present invention. It should be understood, however, that the invention is not limited to the specific details of the Example.

EXAMPLE 1

A mixture of 2.00 grams (4.92 millimoles) of bis-(p-carboxyphenyl) terephthalate and 20 milliliters of thionyl chloride is refluxed under argon for two hours. The excess thionyl chloride is removed by vacuum distillation. A mixture of 0.56 grams (10 mmoles) of propargyl alcohol, 1.01 grams (10 mmoles) of triethylamine and 50 milliliters of chloroform is added to the residue obtained. The resulting mixture is stirred under argon at room temperature overnight. The chloroform solution is washed with 50 milliliter portions of aqueous 10 percent hydrochloric acid, water and evaporated under vacuum to give a light yellow solid. Recrystallization from chloroform yields 1.89 grams (79.7 percent yield) of bis-(p-carbepropynoxyphenyl)terephthalate.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. Heat-curable acetylene-terminated monomers capable of forming an anisotropic melt phase of the formula:

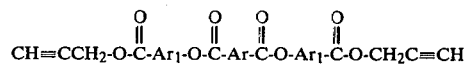

wherein Ar is a divalent radical comprising at least one aromatic ring and Ar₁ is a divalent radical selected from the group consisting of phenylene, naphthylene, biphenylene and mixtures thereof with at least some of the hydrogen atoms present upon the aromatic rings in said divalent radicals optionally being replaced by substitution selected from the group consisting of an alkyl group of 1 to 4 carbon atoms, an alkoxy group of 1 to 4 carbon atoms, halogen, phenyl and mixtures thereof.

2. A heat-curable monomer of claim 1 wherein Ar is selected from the group consisting of

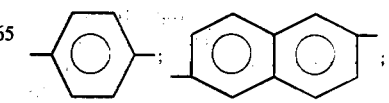

-continued

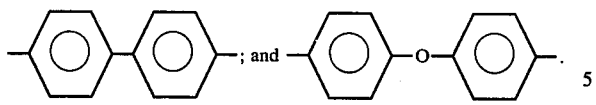

3. A heat-curable monomer of claim 1 wherein Ar is

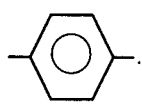

4. A heat-curable monomer of claim 1 wherein Ar is

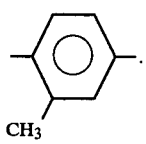

5. A heat-curable monomer of claim 1 wherein Ar is

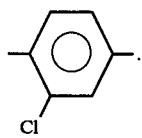

6. A heat-curable monomer of claim 1 wherein Ar is

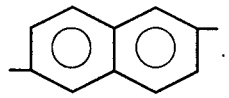

7. A heat curable monomer of claim 1 wherein Ar is

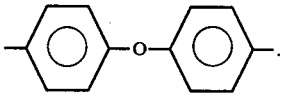

8. A heat-curable monomer of claim 1 wherein Ar is

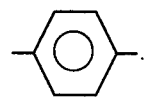

9. A heat-curable monomer of claim 1 wherein $Ar_1$ is

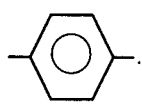

10. Bis(p-carbepropynoxyphenyl)terephthalate.
11. A thermoset resin comprised of a monomer of claim 1.
12. A thermoset resin comprised of a monomer of claim 10.

* * * * *